United States Patent [19]

Nishida et al.

[11] 4,282,438
[45] Aug. 4, 1981

[54] COMPUTED TOMOGRAPHY APPARATUS AND METHOD USING PENETRATING RADIATION

[75] Inventors: Susumu Nishida, Yokohama; Tamon Inouye, Kawasaki; Tadatoki Yoshida, Tokyo; Kiyoto Saito, Yokohama, all of Japan

[73] Assignee: Tokyo Shibaura Electric Co., Ltd., Japan

[21] Appl. No.: 877,730

[22] Filed: Feb. 14, 1978

[30] Foreign Application Priority Data

Feb. 14, 1977 [JP] Japan .................. 52-14116

[51] Int. Cl.$^3$ ............................. G01N 21/00
[52] U.S. Cl. ................ 250/445 T; 250/360; 250/363 S
[58] Field of Search .............. 250/445 T, 360, 363 S

[56] References Cited

U.S. PATENT DOCUMENTS

| | | | |
|---|---|---|---|
| 2,667,585 | 1/1954 | Gradstein | 250/445 T |
| 4,031,395 | 6/1977 | Le May | 250/360 |
| 4,045,672 | 8/1977 | Watanabe | 250/360 |
| 4,071,769 | 1/1978 | Brunnett et al. | 250/445 T |
| 4,138,721 | 2/1979 | Boyd | 250/445 T |

Primary Examiner—Alfred E. Smith
Assistant Examiner—Thomas P. O'Hare
Attorney, Agent, or Firm—Finnegan, Henderson, Farabow, Garrett and Dunner

[57] ABSTRACT

A computerized tomography system and method using penetrating radiation having a radiation source for radiating penetrating radiation into the interior of a thin sliced layer portion of a subject, in a manner that it expands substantially in a fanned fashion, a detector for substantially dividing the radiation after passing through said sliced layer portion into a plurality of radiation beams diverging at a defined angle, thereby detecting the intensity of said beams, a moving unit for substantially linearly scanning each of said beams at least once in a direction transverse of said sliced layer portion, a data processing unit for reconstructing an image of said sliced layer portion on the basis of detected data delivered from said detector, and a display unit for displaying said image on the basis of the results of said reconstruction.

10 Claims, 8 Drawing Figures

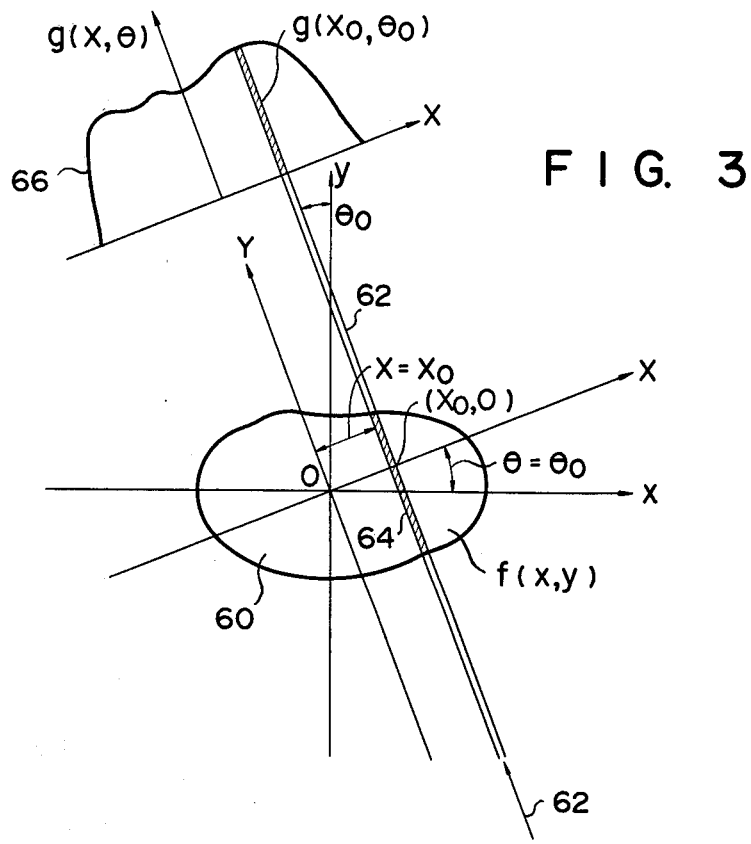
FIG. 3
FIG. 4
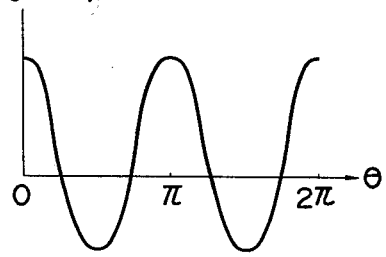
FIG. 5
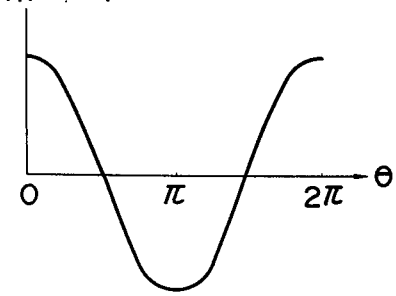

F I G. 7
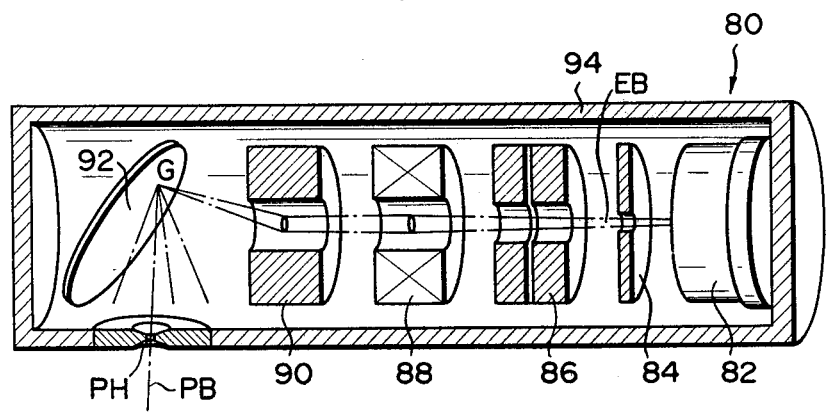
F I G. 8
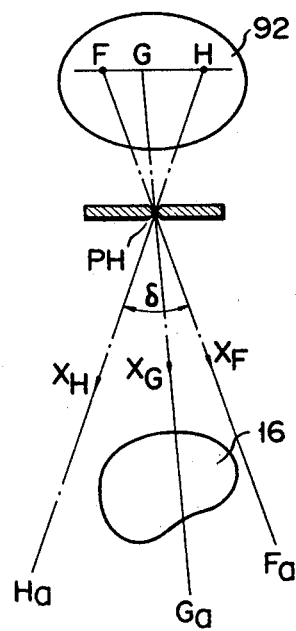

COMPUTED TOMOGRAPHY APPARATUS AND METHOD USING PENETRATING RADIATION

This invention relates to an apparatus and method for tomography using penetrating radiation comprising a radiation source for radiating penetrating radiation into the interior of a sliced layer portion to be displayed of a human body in a manner that it expands substantially in a fanned fashion, a detector for substantially dividing the radiation which has passed through the sliced layer portion into a plurality of radiation beams diverging at a defined angle, thereby detecting the intensity of said beams, a moving unit for scanning said beams so as to scan said sliced layer portion, a data processing unit for reconstructing an image of said sliced layer portion on the basis of the detected data delivered from said detector, and a display unit for displaying said image on the basis of the results of said reconstruction.

Apparatus for tomography using penetrating radiation, i.e. X rays or gamma rays has been generally known, and typical examples of such apparatus include various types of CT (Computed Tomography) systems used to reconstruct and display the image of a sliced layer portion defined in a subject through data processing using a computer. Such a CT apparatus requires projection data related to the transmission path of the radiation, and the projection data can be obtained by projecting the radiation beam into the subject from a plurality of different directions. It is to be noted, therefore, that in obtaining the desired tomogram, the radiation source and at least one detector for measuring the intensity of the beam passing through the sliced layer portion have to be rotated at least 180 degrees around the subject to obtain the necessary projection data. To perform the above mentioned measurement a circular track is provided in a CT scanner on which the radiation source and detector are mounted, and a rotary mechanism is additionally provided to rotate the CT scanner around the subject at least 180 degrees. At that time the subject is supported in a central opening within the track. Consequently the dimensions of the sliced layer portion to be displayed may be comparatively small so as not to be affected by the size of the central opening and/or the subject. For displaying a large sliced layer portion, a very large rotary mechanism must be provided in the case of a conventional apparatus. The diameter of the central opening may measure up to 80 cm maximum, and generally is at least 25 to 45 cm approximately, therefor even if the sliced layer portion to be displayed is a relatively small portion or portion having a short length along the longitudinal axis of the subject, it may be impossible to display such portion directly.

An object of the invention is to provide an apparatus and method for tomography using penetrating radiation capable of easily displaying a large sliced layer portion of a subject or its partial region without the above defects exhibited by conventional CT apparatus.

In order to attain the above object, the moving unit of the apparatus for tomography of this invention has a construction permitting at least one substantially linear scanning of each said beams in a direction transverse of said sliced layer portion, which linear scanning is carried out while keeping intact a corresponding one of plural projection directions falling within the range of fan-shaped expression of said beams.

In this apparatus, as the radiation beams or projecting beams constructing a radiation projected from the radiation source expanding in a fan shape are shifted substantially linearly in a direction transverse of said sliced layer portion, linear scanning for said portion is carried out while keeping intact a corresponding one of plural projecting directions falling within the range of fan-shaped expression of said beams. Therefore, if the expanding angle of the radiation is indicated by $\alpha$, the projection data computed on the basis of the detected data obtained by the detector may be substantially the same as the projection data obtained when the scanner having a radiation source projecting a plurality of parallel pencil beams for parallel scanning is rotated around the subject by $\alpha$ degree and the intensities of the beams are measured in an appropriate position on the path of rotation. The above value $\alpha$ may be determined in accordance with the property and size of the sliced layer portion, sharpness of the image required for display and other factors, and in practice it is selected to be less than 180 degrees, preferably approximately 20 to 30 degrees.

According to the apparatus of this invention, as a desired image to be displayed can be obtained only by substantially linearly shifting the radiation beams with respect to the subject, therefore, the construction of the scanner can be simplified, and the projection data necessary for obtaining an image of the slice which is selected in the subject along the longitudinal axis of the subject and its partial region can be collected in a short time.

According to a preferred embodiment of this invention, the moving unit has a rack and pinion mechanism with the rack mounted along the moving direction of a frame on which the radiation source and detector are mounted. In such arrangement, the radiation source and detector can be moved by a known and simple mechanism.

According to another preferred embodiment of the invention, an X ray generating unit or an X ray pencil beam generator for rocking an X ray pencil beam in a fan shape is employed as the radiation source. In such construction, a desired image can be obtained by a known radiation source, and the X ray pencil beam generator may be able to reduce the radiation dose exposed to the subject or human body.

In a still another preferred embodiment of the invention, the data processing unit for reconstructing the image of the sliced layer portion based on the detected data transmitted from the detector comprises a projection data calculating unit for computing the projection data related to the transmission path of the radiation beams respectively from the detected data projected from the detector and a basic data calculating unit comprising a first calculating unit for computing the one-dimensional Fourier transform of the projection data related to the respective projecting directions of the radiation beams from the above projection data and a second calculating unit for computing the one-dimensional Fourier transform with respect to directions selected about the full circumference of the sliced layer portion on the basis of the above Fourier transform computed by the first calculating unit which relates to the radiating directions included in the expanding range of the radiation beams, and an image reconstruction unit comprising a third calculating unit for computing the two-dimensional Fourier transform of the absorption coefficient distribution of the sliced layer portion depending upon the one-dimensional Fourier transform transmitted from the basic data processing unit and an inverse Fourier transform unit for computing the absorption coefficient distribution of the sliced layer portion by applying the two-dimensional inverse Fourier transformation for the above two-dimensional transform computed by the third calculating unit. By utilizing the data processing unit as described above, the absorption coefficient distribution of the sliced layer portion can be computed, based on the detected data obtained in the range of the angle α by using the detector to display the computed results in the display unit.

This invention can be more fully understood from the following detailed description when taken in conjunction with the accompanying drawings, in which:

FIG. 3 is a diagrammatic view illustrating a process forming a projection profile by means of the X ray beam projected through the sliced layer portion;

FIG. 4 is a graph illustrating the periodicity of the real part included in a one-dimensional Fourier transform calculated from the projection profile, in which the real part is shown as a function of the projecting angle $\theta$.

FIG. 5 is a graph illustrating the periodicity of the imaginary part included in the one-dimensional Fourier transform calculated from the projection profile, in which the imaginary part is shown as a function of the projecting angle $\theta$;

FIG. 7 is a cross sectional view of an X ray pencil beam generator; and

FIG. 8 is a schematic diagram illustrating a process for generating a substantially fan-shaped X ray beam projected from the X ray pencil beam generator of FIG. 7.

FIG. 1 is a view schematically illustrating the construction and operation of one embodiment of this invention utilizing an X ray source for generating penetrating radiation.

Figure 1:
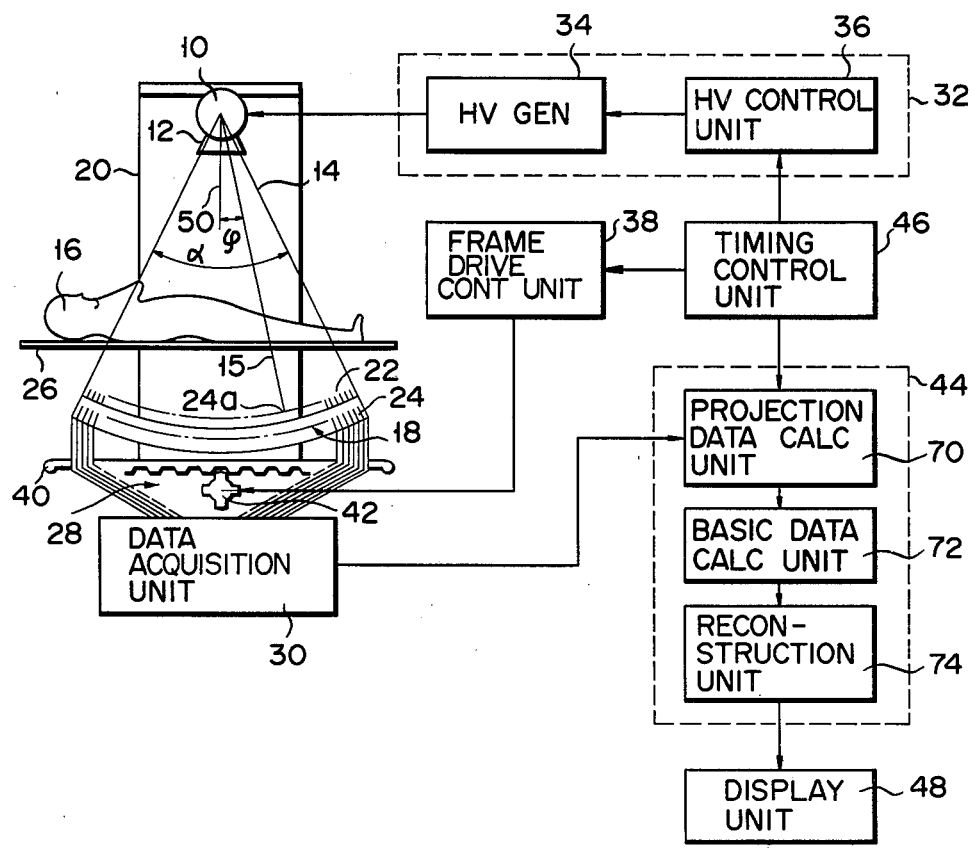
FIG. 1 illustrates one embodiment of a computed tomography system using an X ray source according to the invention.

There are illustrated in FIG. 1 an X ray tube 10 used for a radiation source, a radiation source collimator 12 for transforming the X-rays radiated from the tube 10 into a substantially fan-shaped X ray bearing a subject or human body 16 to be examined by the apparatus of this invention, an X ray detector 18 provided opposite to the tube 10, whereupon the subject 16 is located between the detector 18 and tube 10, a frame 20 having thereon the tube 10 and detector 18 and linearly movable longitudinally of the human body 16, a bank of detector-collimators 22 corresponding to the bank of detecting elements 24 forming the detector 18, a bed 26 supporting the body 16 firmly, a scanning unit 28 for linearly moving the frame 20 in parallel with the sliced layer portion, and a data acquisition unit 30 for collecting the detected data transmitted from the detecting elements 24.

An X ray source control unit 32 is provided to control the operation of the X ray tube 10, including a high voltage generator 34 for driving the tube 10 and a high voltage source control unit 36 for controlling the X ray generation. The scanning unit 28 is controlled by a frame drive control unit 38, and moves the frame 20 in the plane of the paper. In the embodiment shown, the frame 20 can be driven by a rack 40 attached to the lower end thereof and a pinion 42 engaging with the former and driven by the frame drive control unit 38. When the frame 20 is moved, the data acquisition unit 30 collects all data on the intensity of the X rays passing through the human body, obtained by each detecting element 24 at predetermined positions and transmits them to a data processing unit 44. The X ray source control unit 32, frame drive control unit 38 and data processing unit 44 are operated in accordance with timing signals transmitted from a timing control unit 46. The data processing unit 44 is operated to compute the data on the beam intensity obtained responsive to appropriate signals timing and transmitted from the data acquisition unit 30. The unit 44 also functions to group the projection data related to selected projecting directions within the diverging angle region of the fan-shaped beam 14 and is operated to calculate the basic data i.e. one-dimensional Fourier transform based on the above projection data with respect to substantially all the directions necessary for reconstruction of the image of the scanned sliced layer portion and is further operated to reconstruct the image from the foregoing basic data. The image may be displayed on the display unit 48 in accordance with the calculated basic data. The projection data and basis data will be described later.

Figure 2:
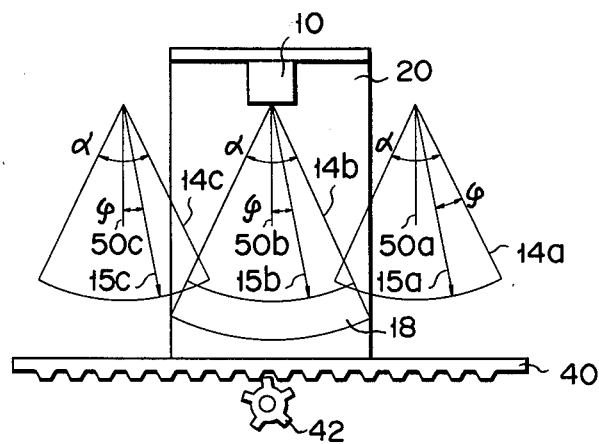
FIG. 2 is a schematic diagram illustrating a condition obtained by linear movement of the fan-shaped radiation beam shown in FIG. 1.

FIG. 2 is a view illustrating the manner in which the fan shaped X ray beam 14 radiated from the tube 10 moves together with the detector 18 and the frame 20 along a scanning path parallel to the plane of the beam 14 and to the plane of the paper. For simplicity only three positions 14a, 14b and 14c of the fan-shaped X ray beam are shown in FIG. 2.

As shown in FIG. 1, the plurality of detecting elements 24 are arranged on a circumferential arc about the tube 10 so as to be opposed to the X ray tube 10, and each detecting element 24 detects a predetermined portion of the fan-shaped X ray beam 14 received at a different projection direction. It is, therefore, understood that the fan-shaped X ray beam 14 may be considered as comprising a number of individual X ray pencil beams equal to the number of detecting elements 24 located about the tube 10 in the region of the angle α. There is shown in FIG. 1 the X ray individual beam 15 which may be projected toward a detecting element 24a provided at a position making an angle φ with the vertical line 50 perpendicular to the bed 26. The beam 15 is indicated in the fan-shaped beams 14a, 14b and 14c by 15a, 15b and 15c respectively as shown in FIG. 2. It may be understood from FIG. 2 that, when the fan-shaped X ray beam is moved by driving the frame 20, the human body 16 (not shown in FIG. 2) on the bed 26 is scanned in the longitudinal direction by the pencil beam 15 projected at the angle φ to the vertical line 50. All the other X ray individual pencil beams received by the other detecting elements 24 can be used to scan the human body 16 in the same plane as the beam 15, therefore, if the X ray beams having different projection directions are detected at various positions during one linear traverse of the frame 20, it is possible to obtain projection data representing the intensities of the X ray beams, which is equivalent to that which would be obtained when the longitudinal slice parallel to the plane of the paper is rotationally scanned through an angle α by a plurality of parallel X ray beams also projected in the plane of the paper.

Description will be made below of the principal theory and units for reconstructing an image of a sliced longitudinal layer portion of the body 16, based on the detected projection data transmitted from the data acquisition unit 30 to the data processing unit 44.

The detected data from one detector 24 indicates the intensity of an X ray beam, determined by the integral value of the X ray absorption coefficients lying along each transmission path. In the apparatus of the invention, the projection data determined by the integral value of the X ray absorption coefficients is initially calculated based on the detected data. And thereafter, the absorption coefficient distibution in the sliced layer portion i.e. the image of the sliced layer portion, is calculated or reconstructed. When the absorption coefficient distribution can be calculated by the process as described above, the image may be visually displayed in the display unit based on the distribution in accordance with known display techniques. The display unit here described includes a printer for typing out the data representing the reconstructed image.

Various means have been proposed with regard to the image reconstruction method, in which the methods mainly used are the Convolution method, the Filtered Back Projection Method and the Fourier Transform Method. These methods are different from each other in a representation or practical data processing aspect, but on the other hand, they are not different in an arithmetic aspect, therefore, one exemplary embodiment utilizing the Fourier transform Method will be described below.

The theory of the Fourier transform method is hereafter described referring to FIG. 3. There is illustrated in FIG. 3 sliced layer portion 60 of the human body to be reconstructed, which is parallel with the plane of the paper. There is established on the surface of the sliced layer portion 60 a rectangular coordinate system (x, y) having an origin O fixed to the above sliced portion. 62 indicates an X ray beam passing through the sliced layer portion. Also shown in FIG. 3 is a rectangular coordinate system (X, Y) also having the common origin O, whose X axis extends perpendicular to the transmission direction of the X ray beam 62 and makes an angle $\theta$ with the x axis. The Y axis, therefore, extends in a direction parallel to the X ray beam. Since the angle $\theta$ is varied according to the projecting direction of the beam 62, the value of $\theta$ for the X ray beam 62 is set at $\theta_0$ for clarifying the description. A X distance from a position at which the X ray beam 62 travels across the X axis i.e. the distance from the origin O to X ray beam 62, is set at $X_0$, f(x, y) in FIG. 3 is an absorption coefficient, at an optional point (x, y) on sliced section 60.

Bar graph $g(X_0, \theta_0)$ drawn at the upper portion of the transmission path of the X ray beam 62 which has passed through the sliced layer portion 60 is the projection data calculated from the detected data of the detecting element (not shown) related to the transmission path 64 of the X ray beam 62.

In FIG. 3, there is illustrated only one projection data point $g(X_0, \theta_0)$ related to X ray beam 62 determined by the both values of $\theta_0$ and $X_0$. However, a plurality of projection data points related to the transmission paths of beams parallel to the X ray beam 62 can be obtained by the substantially linear movement of the frame 20 (FIG. 1). The values for all projection data points can be described by a function of $\theta$ and X as shown in the figure. Therefore, it is ordinarily indicated as $g(X, \theta)$. The respective values can be indicated as bar graphs similar to $g(X_0, \theta_0)$ in the coordinate system including the transverse axis X and vertical axis $g(X, \theta)$, but for simplicity, the bar graphs of the individual respective $g(X, \theta)$ points are omitted and only the curve obtained by connecting the top end of each bar graph i.e. the projection profile or envelope 66 of the sliced layer portion 60 (simply called "projection of the sliced portion") is shown in FIG. 3.

The one-dimensional Fourier transform $G(\omega, \theta)$ related to the X of the above projection profile 66 is calculated by the following equation.

$$G(\omega, \theta) = \int_{-\infty}^{\infty} g(X, \theta)e^{-i\omega X}dX \quad (1)$$

Where, $g(X, \theta)$ is the above projection profile 66 and $\omega$ is a spatial frequency ordinarily introduced to obtain the Fourier transform. Assume that the absorption coefficient distribution f(x, y) of the sliced layer plane 60 is known. A two-dimensional Fourier transform $F(\xi, \eta)$ related to x and y is determined from the data of f(x, y). The equation for calculating $F(\xi, \eta)$ based on f(x, y) is written as follows;

$$F(\xi, \eta) = \int_{-\infty}^{\infty}\int_{-\infty}^{\infty} f(x, y)e^{-i(\xi x+\eta y)}dxdy \quad (2)$$

Where $\xi$ and $\eta$ are a spatial frequency which are new variables introduced to obtained the two-dimensional Fourier transform.

Successively, $F(\xi, \eta)$ is converted to $F(\omega, \theta)$ represented in a polar coordinate reference by using the following equations (3) for $\xi$ and $\eta$ of $F(\xi, \eta)$;

$$\xi = \omega \cos\theta \quad (3)$$
$$\eta = \omega \sin\theta$$

By making use of the theorem stating that the one-dimensional Fourier transform of the projection (projection profile) $g(X, \theta)$ of a certain reconstruction image f(x, y) is equal to the central section, i.e. the section containing the original point, provided by cutting at a corresponding angle the two-dimensional Fourier transform of that image f(x, y), the following equation (4) can be obtained;

$$F(\omega\cos\theta, \omega\sin\theta) = G(\omega, \theta) \quad (4)$$

The foregoing central section is a section crossing the origin of the frequency region, i.e. the position satisfying the equation $\omega = 0$.

Accordingly, if $G(\omega, \theta)$ obtained by equation (1) may be converted to the ($\xi, \eta$) coordinate system by using equation (3), it is equal to $F(\xi, \eta)$ obtained by transforming $F(\omega, \theta)$ to the ($\xi, \eta$) coordinate system, as being understandable from the equation (4).

It is to be understood based on the above equations that $G(\omega, \theta)$, i.e. $F(\xi, \eta)$, for the various values of $\theta$ appropriately selected in the range expanding over the full circumference about 360 degrees of the human body 16 and calculated by a method described below can be computed based on the various projection data $g(X, \theta)$ calculated from the intensity data obtained from all the detecting elements 24 and obtained by linearly scanning the fan-shaped X ray beam 14 as shown in FIGS. 1 and 2.

The absorption coefficient, consequently, absorption coefficient distribution in each point (x, y) of the sliced layer portion 60 is obtained by applying two-dimensional inverse transformation to $F(\xi, \eta)$ by the following equation;

$$f(x, y) = \frac{1}{4\pi^2} \int_{-\infty}^{\infty}\int_{-\infty}^{\infty} F(\xi, \eta)e^{i(\xi x + \eta y)}d\xi d\eta \quad (5)$$

As seen in the above equations, it is noted that in the image reconstruction method described above, the itensity data of the X ray beam for the various values of $\theta$ selected over the full circumference of 360 degrees is absolutely required, but the desired intensity data over 360 degrees, i.e., the projection profile 66 (FIG. 3), can not be obtained by linearly moving the X ray tube 10 and detecting elements 24 as described in the invention. In this case, only the intensity data measured in the range of the expanding angle $\alpha$ of the fan-shaped X ray beam 14 may be obtained.

According to the invention, however, the projection data $g(X, \theta)$ and one-dimentional Fourier transform $G(\omega, \theta)$ (depending on equation (1)) within the above angle $\alpha$ region are detected and calculated in turn based on the intensity data related to $\theta$ in the above $\alpha$ angle region, and then the equation for calculating $G(\omega, \theta)$ related to all directions within the full 360° range is determined based on $G(\omega, \theta)$ for the value of $\theta$ selected in the angle $\theta$. $G(\omega, \theta)$ related to the full 360° range is computed by the above equation, to calculate $F(\xi, \eta)$ corresponding to $G(\omega, \theta)$, and finally the image of the sliced layer portion is reconstructed and displayed based on the equation (5).

The above equation for calculating $G(\omega, \theta)$ for the full range of angles can be obtained by making use of the fact that $G(\omega, \theta)$ is a periodic function of $\theta$. This will be described below.

Equation (2) can be initially transformed to the following;

$$F(\xi, \eta) = \int_{-\infty}^{\infty}\int_{-\infty}^{\infty} f(x, y)[\cos(\xi x + \eta y) - i\sin(\xi x + \eta y)]dxdy \quad (6)$$

As apparent from the equation (6), the function $F(\xi, \eta)$ includes the real part $ReF(\xi, \eta)$ and the imaginary part $ImF(\xi, \eta)$.

The following is here written;

$$ReF(\xi, \eta) = \int_{-\infty}^{\infty}\int_{-\infty}^{\infty} f(x, y)\cos(\xi x + \eta y)dxdy \quad (7)$$

$$ImF(\xi, \eta) = -\int_{-\infty}^{\infty}\int_{-\infty}^{\infty} f(x, y)\sin(\xi x + \eta y)dxdy$$

$$ReF(-\xi, -\eta) = \int_{-\infty}^{\infty}\int_{-\infty}^{\infty} f(x, y)\cos(-\xi x, \eta y)dxdy \quad (8)$$

$$= \int_{-\infty}^{\infty}\int_{-\infty}^{\infty} f(x, y)\cos(\xi x + \eta y)dxdy$$

$$= ReF(\xi, \eta)$$

Similarly, $$ImF(-\xi, -\eta) = -\int_{-\infty}^{\infty}\int_{-\infty}^{\infty} f(x,y)\sin(-\xi x - \eta y)dxdy \quad (9)$$

$$= \int_{-\infty}^{\infty}\int_{-\infty}^{\infty} f(x,y)\sin(\xi x + \eta y)dxdy$$

$$= -ImF(\xi, \eta)$$

The following equations may be derived from the equation (3):

$$-\xi = -\omega\cos\theta = \omega\cos(\theta + \pi)$$

$$-\eta = -\omega\sin\theta = \omega\sin(\theta + \pi)$$

Accordingly, the equations (8) and (9) can be expressed with the values $\omega$ and $\theta$ as follows;

$$ReF(\omega\cos(\theta + \pi), \omega\sin(\theta + \pi)) = ReF(\omega\cos\theta, \omega\sin\theta)$$

$$ImF(\omega\cos(\theta + \pi), \omega\sin(\theta + \pi)) = -ImF(\omega\cos\theta, \omega\sin\theta)$$

$G(\omega, \theta)$ can be also expressed with the real part $ReG(\omega, \theta)$ and the imaginary part $ImG(\omega, \theta)$, therefore, based on equation (4), the following equations (10) and (11) can be written as follows;

$$ReG(\omega, \theta + \pi) = ReF(\omega\cos(\theta + \pi), \omega\sin(\theta + \pi)) \quad (10)$$
$$= ReF(\omega\cos\theta, \omega\sin\theta)$$
$$= ReG(\omega, \theta)$$

similarly, $$ImG(\omega, \theta + \pi) = ImF(\omega\cos(\theta + \pi), \omega\sin(\theta + \pi)) \quad (11)$$
$$= -ImF(\omega\cos\theta, \omega\sin\theta)$$
$$= -ImG(\omega, \theta)$$

It is, therefore, understood that the value for the equal $\omega$ of $G(\omega, \theta)$ has the periodicity with regard to the value $\theta$. As seen from the equation (10), the real part $ReG(\omega, \theta)$ is a periodic function of $\theta$ i.e. $\pi$, and also as seen from the equation (11), $ImG(\omega, \theta)$ is a periodic function of $\theta$ whose sign may be reversed every $\pi$, and may be returned to the original sign by variation of $2\pi$. FIG. 4 indicates the relationship between $ReG(\omega, \theta)$ and $\theta$. FIG. 5 indicates the relationship between $ImG(\omega, \theta)$ and $\theta$.

Since the function $G(\omega, \theta)$ is a periodic function as mentioned above, $ReG(\omega, \theta)$ and $ImG(\omega, \theta)$ can be developed in the form of an infinite Fourier series expansion respectively.

$$ReG(\omega,\theta) = \sum_{n=0}^{\infty}[An(\omega)\cos 2n\theta + Bn(\omega)\sin 2n\theta] \quad (12)$$

$$ImG(\omega,\theta) = \sum_{n=0}^{\infty}[Cn(\omega)\cos(2n + 1)\theta + Dn(\omega)\sin(2n + 1)\theta] \quad (13)$$

$ReG(\omega, \theta)$ and $ImG(\omega, \theta)$ can be calculated with the sufficient accuracy by summing up the terms of these functions until a term number n reach a properly selected one in accordance with the desired accuracy, because the values of the coefficients $An(\omega)$, $Bn(\omega)$, $Cn(\omega)$ and $Dn(\omega)$ approach zero as the term number n is increased.

The following equations (14) and (15) are utilized in place of the equations (12) and (13), respectively.

$$ReG(\omega,\theta) \approx \sum_{n=0}^{N} [An(\omega)\cos 2n\theta + Bn(\omega)\sin 2n\theta] \quad (14)$$

$$ImG(\omega,\theta) \approx \sum_{n=0}^{N} [Cn(\omega)\cos(2n + 1)\theta + Dn(\omega)\sin(2n + 1)\theta] \quad (15)$$

In order to evaluate the aforesaid coefficients, a number K is defined which is selected according to the equation below.

$$K \geq 2(N+1)$$

Then the Fourier transforms $G(\omega, \theta_1)$, $G(\omega, \theta_2)$ ... $G(\omega, \theta_k)$ of the projection profiles $g(X, \theta_1)$, $g(X, \theta_2)$ ... $g(X, \theta_k)$ related to the angles $\theta_1, \theta_2 \ldots \theta_k$ are calculated on the basis of equation (1). Angles $\theta_1, \theta_2 \ldots \theta_k$ are selected in the angle range of $0 \leq \theta \leq \alpha$. Accordingly, the values $\theta_1, \theta_2 \ldots \theta_k$ are substituted in turn into the right sides of the equation (14), and (15) and the values of the real part $ReG(\omega, \theta_1)$, $ReG(\omega, \theta_2) \ldots ReG(\omega, \theta_k)$ and the imaginary parts $ImG(\omega, \theta_1)$, $ImG(\omega, \theta_2) \ldots ImG(\omega, \theta_k)$ of $G(\omega, \theta_1)$, $G(\omega, \theta_2) \ldots G(\omega, \theta_k)$ for various values of $\omega$ are substituted in turn into the left sides thereof to obtain linear simultaneous equations with respect to the coefficients $An(\omega)$, $Bn(\omega)$, $Cn(\omega)$ and $Dn(\omega)$, therefore, the various coefficients shown above can be computed by solving the above equations. Consequently, after substituting the values of the coefficients in the equations (14) and (15), $G(\omega, \theta)$ for the desired $\omega$ and $\theta$ can be computed depending upon the equation (14) and (15). Each $G(\omega, \theta)$ thus computed is used for the basic data for reconstructing the image of sliced layer portion. The elements of the data processing unit 44 shown in FIG. 1 include a projection data calculating unit 70, basic data calculating unit 72 and image reconstruction unit 74. The various circuits such as a memory, gates and others for smoothly operating the above units 70, 72 and 74 are provided in the data processing unit 44, but such auxiliary means or control means, being well known are omitted to illustrate the most significant means 70, 72 and 74 in FIG. 1.

The projection data calculating unit 70 receives the detected data from the data acquisition unit 30 and calculates the projection data $g(X, \theta)$ corresponding to the detected data. The basic data calculating unit 72 receives the projection data $g(X, \theta)$ ($0 \leq \theta \leq \alpha$) and classifies these data in groups according to each projection direction, i.e. each projection angle, and computes the Fourier transform $G(\omega, \theta)$ with respect to the angle $\theta$ within the range $0 \leq \theta \leq \alpha$ based on the actually measured projection data while calculating the coefficients of the one-dimensional Fourier expansion series defined in equations (14) and (15) so as to obtain the values corresponding to the Fourier transform $G(\omega, \theta)$ with respect to the angle $\theta$ within the range $\alpha < \theta \leq 2\pi$ following the above process, based on the Fourier transform $G(\omega, \theta)$ data obtained by the actually measured data. The image reconstruction unit 74 obtains the two-dimensional Fourier transform $F(\xi, \eta)$ from a substantially one-dimensional Fourier transform of the projection data over the full circumference of this sliced layer portion which derived from the one-dimensional Fourier transform $G(\omega, \theta)$ ($0 \leq \theta \leq \alpha$), and the one-dimensional Fourier expansion series. The image reconstruction unit 74 also calculates the two-dimensional inverse Fourier transform of the $F(\xi, \eta)$ to reconstruct the $f(x, y)$ i.e., the image of the sliced layer portion of the subject.

Figure 6:
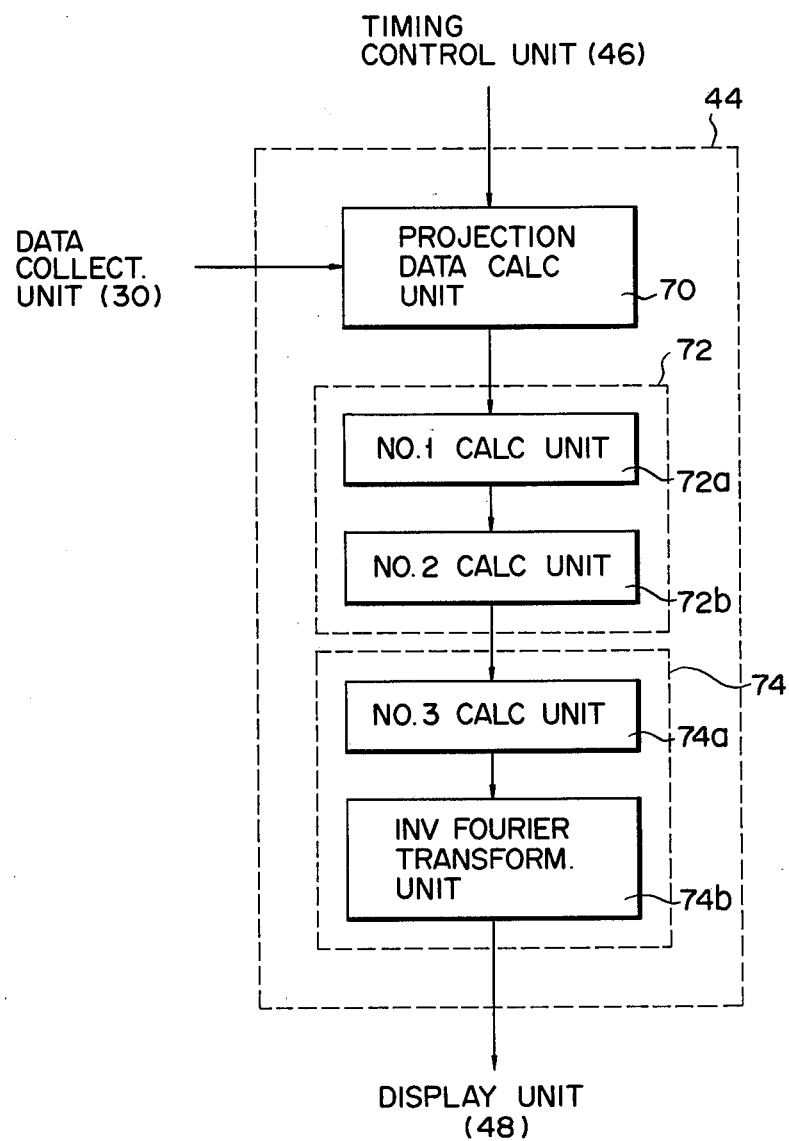
FIG. 6 is a block diagram illustrating the detailed construction of the data processing unit 44 shown in FIG. 1.

FIG. 6 illustrates the data processing unit 44 in more detail. There is illustrated in FIG. 6 further the basic data calculating unit 72 having therein a first calculating unit 72a for calculating a first one-dimensional Fourier transform $G(\omega,\theta)$, ($0 \leq \theta \leq \alpha$) based on the projection data of $g(X,\theta)$, ($0 \leq \theta \leq \alpha$); obtained by actual measurement and a second calculating unit 72b for calculating a second coefficients of one-dimensional Fourier expansion series defined in equations (14) and (15) on the basis of the fact that the first one-dimensional Fourier transform $G(\omega,\theta)$, ($0 \leq \theta \leq \alpha$) has a periodicity over $2\pi$ radians with respect to the projection direction. There is illustrated also in FIG. 6 the image reconstruction unit 74 provided with a third calculating unit 74a for obtaining the two-dimensional Fourier transform $F(\xi,\eta)$—; of the absorption coefficient distribution $f(x,y)$—; of the sliced layer portion 60 from the output data of $G(\omega,\theta)$, ($0 \leq \theta \leq \alpha$) and $G(\omega,\theta)$, ($\alpha \leq \theta \leq 2\pi$) the basic data calculating unit 72, and a two-dimensional inverse Fourier transform unit 74b for calculating the absorption coefficient distribution $f(x,y)$ of the sliced layer portion 60 from the two-dimensional Fourier transform $F(\xi,\eta)$.

It is described in the embodiment mentioned above that the X ray beam radiated from the X ray source 10 is formed into the fanshaped X ray beam 14 by the radiation source collimater 12, which beam is projected to the human body 16 to be examined. A substantial similar fan-shaped X ray beam may be obtained by other means, for example, an X ray pencil beam generator (also called an "X ray microbeam generator") for rocking the pencil beam through a sector (also called an "X ray microbeam") in a fan shape.

The above X ray pencil beam generator 80 is illustrated in FIG. 7. The electron beam EB projected from an electron gun 82 may be accelerated by the electric field generated by the high voltage applied to an anode 84, and may be formed in a predetermined shape by an alignment coil 86 and a, focusing coil 88 to be transmitted through a deflection lens or deflection coil 90. The deflection voltage applied to coil 90 is varied in accordance with a predetermined program controlled by an electronic computer (not shown). The deflection voltage determines the hit point G at which beam EB impinges on a target 92. The target 92 made by heavy metal for X ray generation. Then the target 92 obliquely located to the axis of the series of substantially aligned members from the electron gun 82 to the deflection coil 90. An X ray beam is emitted from the hit point G when the electron beam EB hits the target 92, and part of the emitted X rays pass through a pin hole PH provided in the casing 94 and form the X ray pencil beam PB which is projected to the human body 16.

FIG. 8 is a system diagram for substantially generating a fan-shaped X ray beam utilizing the X ray pencil beam generator 80. In FIG. 8 the members necessary to explain the above generating system and the human body 16 are illustrated, and the target 92 is indicated as a side view which is viewed from the right side of the generator 80 shown in FIG. 7. The target 92 is positioned at an angle with respect to the electron gun 82. When the electron beam EB is radiated toward the point G in FIG. 7 and FIG. 8, one part of the X ray along the G-Ga line is projected to the body 16 as a pencil beam XG. When the hit point is shifted to a point F by controlling the deflection lens 90 as shown in FIG. 8, a pencil beam $X_F$ travelling along a path F-Fa passing through the pin hole PH is obtained. On the other hand, when the hit point is shifted to the point H, it is possible to obtain a pencil beam $X_H$ travelling along the path H-Ha direction. It is accordingly particularly understood that if the hit point is repeatedly shifted within the range from F to H, the pencil beam is repeatedly rocked or scanned within the by angle δ, therefore this results in the same effect as that obtained when an X ray beam extending in a fan shape is radiated to the body 16 to be examined. Accordingly, instead of using the X ray source 10 and collimator 12 shown in FIG. 1, the beam generator 80, arranged so that the plane in which the pencil beam is scanned coinsides with the plane of the paper used, whereupon a display of the slice layer portion of the human body 16 can be obtained as previously described. The X ray dose imparted the human body may be reduced strikingly by utilizing the X ray pencil beam generator.

In the embodiment described above, X rays are used as the penetrating radiation. However, the radiation is not limited to the X ray and γ ray is available instead of above mentioned X ray.

It is noted particularly that according to the invention, the tomogram of the human body to be diagnosed will be achieved simply by linearly moving the radiation beam without revolving it about the human body and therefore the method is utilized easily to obtain the image reconstruction and display of a large sliced layer portion, or a long sliced layer portion, for example the full sliced layer portion or partial region thereof extending along the longitudinal axial direction of a human body, only with the linear movement of the radiation beam or beams as described above. The reconstruction and display of the image of such a large or extended sliced layer portion cannot be achieved by conventional tomography systems. By using the apparatus of this invention, the three-dimensional size of for example a tumor in the patient may be confirmed on the basis of data contained in various tomograms oriented substantially perendicular to the axial direction of the patient and various ones obtained as hereinafter above described substantially parallel with the axial direction of the patient. By determining the size of the tumor measured in this manner the doctor in charge is readily able to form an effective plan for the treatment. According to the invention, further, the desired tomogram can be obtained simply by moving the scanner linearly, therefore, the mechanism of the scanner can be simplified compared with the conventional mechanism used and this results in improved reliability and reduced cost of the apparatus. Further, as data necessary for obtaining the tomogram can be collected only by the linear movement of the scanner, the data collecting time is shortened to a great extent, and the accordingly the quality of the reconstructed image is generally improved, since movement of the patient during the shortened data-collecting time is generally lessened.

What we claim is:

1. A computed tomography system using penetrating radiation comprising:
    a radiation source for emitting penetrating radiation in a diverging beam pattern subtending an angle into the interior of a thin sliced layer portion of a subject to be examined;
    a detector including detecting elements for dividing the radiation after passing through said sliced layer portion into a plurality of radiation beams penetrating said subject at various projection angles θ within the range $0 \leq \theta \leq \alpha, \alpha < 180°$, thereby to detect the intensity of beam penetrating said sliced layer portion;
    scanning means for scanning said beam along a single substantially linear path in a direction parallel to the plane of said sliced layer portion, thereby obtaining intensity data equivalent to that obtained by radiating said sliced layer portion with parallel beams of radiation orbitally scanned about said portion through the single θ;
    a data processing unit for producing data for reconstructing an image of said sliced layer portion, said data processing unit including, a projection data calculating unit for computing projection data for each of said parallel radiation beams on the basis of the detected intensity data delivered from said detector for each said set of parallel beams, and a basic data calculating unit for calculating one-dimensional Fourier transforms of said projection data for the respective radiation directions of said radiation beams within the range $0 \leq \theta \leq \alpha, \alpha < 180°$, and one-dimensional Fourier expansion series on the basis of said one-dimensional Fourier transforms in order to obtain substantially one-dimensional Fourier transforms of the projection data over the full circumference of said sliced layer portion;
    an image reconstruction unit for calculating output data of said basic data calculating unit to reconstruct the image of said sliced layer portion; and
    a display unit for displaying the image of said sliced layer portion.

2. The computed tomography system as set forth in claim 1 wherein said image reconstruction unit includes;
    means for obtaining two-dimensional Fourier transforms of the absorption coefficient distribution of said sliced layer portion from the output data of said basic data calculating unit; and
    inverse Fourier transform means for computing the absorption coefficient distribution of said sliced layer portion by applying two-dimensional inverse Fourier transforms to said two-dimensional Fourier transforms.

3. The apparatus as set forth in claim 1 wherein said scanning means includes a frame and a rack and pinion engaged therewith, which rack is oriented in the scanning direction and is affixed to said frame, the latter supporting said radiation source and detector.

4. The apparatus as set forth in claim 1 wherein said radiation source includes an X ray tube.

5. The apparatus as set forth in claim 1 wherein said radiation source comprises an X ray pencil beam generator for scanning an X ray pencil beam through an angular sector.

6. The apparatus as set forth in claim 1 wherein said projection data calculating unit computes the projection data relating to each group of said beams having a common transmission angle on the basis of the detected data delivered from said detector.

7. The apparatus as set forth in claim 6 wherein said basic data calculating unit comprises first calculating means for calculating on the basis of said projection data obtained from said projection data calculating means the one-dimensional Fourier transform of projection data relating to each commonly angled group of said radiation beams and second calculating means for computing the one-dimensional Fourier transform with respect to directions oriented about the full circumference of said sliced layer portion, on the basis of said Fourier transform data generated by said first calculating means.

8. The apparatus as set forth in claim 7, wherein said image reconstruction unit comprises third calculating means for computing the two-dimensional Fourier transform of the absorption coefficient distribution of said sliced layer portion, on the basis of the one-dimensional Fourier transform data supplied from said basic data calculating means and inverse Fourier transform means for computing the absorption coefficient distribution of said sliced layer portion by applying two-dimensional inverse Fourier transformation to said two-dimensional Fourier transform data obtained from said third calculating means.

9. A method of computed tomography for reconstructing an image of a sliced layer portion of a subject under examination comprising the steps of:
- irradiating said sliced layer portion with a fan-shaped beam of radiation subtending an angle $\alpha, \alpha < 180°$;
- detecting said beam of radiation after it has penetrated said sliced layer portion with a plurality of detectors to generate intensity data signals for a plurality of individual diverging radiation beams spread over said angle $\alpha$;
- scanning said fan-shaped beam and said detectors past said layer portion along a single-substantially linear path parallel to the plane of said sliced layer portion to irradiate each segment of said portion with a plurality of radiation beams projected at different angles;
- storing said intensity data signals and grouping them into sets of projection data signals, each said set including the intensity data signals having a common projection angle;
- calculating one-dimensional Fourier transforms for each set of said projection data signals obtained for the beams within said angle $\alpha, \alpha < 180°$, and one-dimensional Fourier expansion series on the basis of said one-dimensional Fourier transforms in order to obtain substantially one-dimensional transforms of the projection data over the full circumference of said sliced layer;
- determining absorption coefficient distribution for the segments within said sliced layer portion by calculating said substantially one-dimensional Fourier transforms; and
- displaying said absorption coefficient distribution to reconstruct an image of said layer portion.

10. The method of computed tomography as set forth in claim 9 wherein said step of determining absorption coefficient distribution includes the steps of:
- obtaining two-dimensional Fourier transforms based on said substantially one-dimensional Fourier transforms, and calculating the absorption coefficient distribution for the segments within said sliced layer portion by applying two-dimensional inverse Fourier transforms to said two-dimensional Fourier transforms.

* * * * *